US007192580B2

(12) United States Patent
Atkins et al.

(10) Patent No.: US 7,192,580 B2
(45) Date of Patent: Mar. 20, 2007

(54) PURGING OF CELLS USING VIRUSES

(75) Inventors: Harold L. Atkins, Orleans (CA); John C. Bell, Ottawa (CA); Conrad J. Heilman, Jr., Landenberg, PA (US); Brian D. Lichty, Kemptville (CA); Robert M. Lorence, Bethesda, MD (US); Michael S. Roberts, Myersville, MD (US); David F. Stojdl, Ottawa (CA)

(73) Assignees: Wellstat Biologics Corporation, Gaithersburg, MD (US); University of Ottawa, Ottawa (CA)

( * ) Notice: Subject to any disclaimer, the term of this patent is extended or adjusted under 35 U.S.C. 154(b) by 0 days.

(21) Appl. No.: 10/717,101

(22) Filed: Nov. 19, 2003

(65) Prior Publication Data

US 2004/0109878 A1 Jun. 10, 2004

Related U.S. Application Data

(63) Continuation of application No. 09/888,626, filed on Jun. 26, 2001, now abandoned.

(60) Provisional application No. 60/214,014, filed on Jun. 26, 2000.

(51) Int. Cl.
*A61K 48/00* (2006.01)
*C12Q 1/70* (2006.01)

(52) U.S. Cl. .................. 424/93.2; 424/93.1; 424/224.1

(58) Field of Classification Search ............... 424/93.1, 424/224.1, 214.1, 93.2; 435/235.1, 363, 435/372, 320.1
See application file for complete search history.

(56) References Cited

U.S. PATENT DOCUMENTS

| 5,677,178 | A | 10/1997 | McCormick |
| 6,136,307 | A | 10/2000 | Lee et al. |
| 2001/0048919 | A1 | 12/2001 | Morris et al. |
| 2002/0006398 | A1 | 1/2002 | Morris et al. |
| 2004/0170607 | A1 | 9/2004 | Bell et al. |
| 2004/0208849 | A1 | 10/2004 | Bell et al. |

FOREIGN PATENT DOCUMENTS

| WO | WO 94/25627 | 11/1994 |
| WO | WO 99/18799 | 4/1999 |
| WO | WO99/18799 A1 * | 4/1999 |
| WO | WO 00/62735 | 10/2000 |
| WO | WO 01/19380 | 3/2001 |
| WO | WO01/19380 | 3/2001 |
| WO | WO 01/83710 | 11/2001 |
| WO | WO 01/83711 | 11/2001 |

OTHER PUBLICATIONS

Kim et al. The Molecular Medicine Today, 1996, pp. 519-527.*
Balachandran et al. J. Virol. 2001, vol. 75, No. 7, pp. 3474-3479, .*
Strong et al. The EMBO J. 1998, vol. 17, No. 12, pp. 3351-3362.*
Seth et al. Cancer Research 1996, vol. 56, No. 6, pp. 1346-1351.*
Robert C. Mellors , Pathogenesis of HIV infection and AIDS published on 1999 at website of Cornell University Medical College: http://edcenter.med.conell.edu/CMMC_pathNotes/HIV_infection/HIV_infection_04.html.*
Wolff et al. Human Gene. Ther. 1998, vol. 9, pp. 2277-2284.*
PDR Electronic Library, Thomson PDR, 2002-2006 att he thomsonhc.com, p. 1-10.*
Osborne et al. The oncologist 2004, vol. 9, pp. 361-377.*
Weber et al. Crit. Rev. Eukaryot Gene Expr. 2000, vol. 10, No. 3-4, pp. 281-302, abstract only.*
2002 Cell Genesys. Inc. website: http://www.cellgenesys.com, Mar. 31, 2005.*
NIH AIDS reagent repository catalog, 2000, p. 3.*
Coulon et al. J. Virol. 1989, vol. 63, No. 8, pp. 3550-3554.*
Rabies Nature History published by CDC, Dec. 2003.*
Stuart, "Autologous Bone Marrow Transplantation for Leukemia", Seminars in Oncology, vol. 20, No. 5, Suppl 6, pp. 40-54, Oct. 1993.
Hammert, et al., "Purging marrow or peripheral blood stem cells for autografting", Current Opinion in Hematology, vol. 4, pp. 423-428, 1997.
Schneidkraut, et al., "The Contribution of Animal Models to the Development of Treatments for Hematologic Revcoevery Following Myeloablative Therapy: A Review", Journal of Hematotherapy, vol. 5, pp. 631-646, 1996.
Rummel, et al., "Future Paradigm for Autologous Bone Marrow Transplantation: Tumor Purging and Ex Vivo Production of Normal Stem and Progenitor Cells", Journal of Hematotherapy, vol. 3, pp. 213-218, 1994.
Kvalheim, et al., "Purging of Tumor Cells from Leukapheresis Products: Experimental and Clinical Aspects", Journal of Hematotherapy, vol. 5, pp. 427-436, 1996.
Bird, et al., "4-Hydroperoxycyclophosphamide purged autologous bone marrow transplantation in non-Hodgkin's lymphoma patients at high risk of bone marrow involvement", Bonne Marrow Transplantation vol. 18, pp. 309-313, 1996.
Hammert, et al., "Purging autologous bone marrow with monoclonal antibodies for transplantation in acute myelogenous leukemia", Blood Reviews, vol. 11, pp. 80-90, 1997.
Villeneuve, "Ex vivo photodynamic purging in chronic myelogenous leukaemia and other neoplasis with rhodamine derivatives", Biotechnol. Appl. Biochem., vol. 30, pp. 1-17, 1999.

(Continued)

*Primary Examiner*—Bruce R. Campell
*Assistant Examiner*—Bao Qun Li
(74) *Attorney, Agent, or Firm*—Lewis J. Kreisler

(57) ABSTRACT

The subject invention relates to viruses that are able to purge (reduce or eliminate) undesirable cells in a mixture of cells. Undesirable cells can include neoplastic cells, cells mediating graft-versus host diseases, and autoimmune cells. The subject invention also relates to the purging of undesirable cells from bone marrow or peripheral blood cell harvests in the treatment of mammals including cancer patients, transplant recipients, and patients with autoimmune disease.

10 Claims, No Drawings

OTHER PUBLICATIONS

Hirai, et al., "Adenovirus p53 Purging for Human Breast Cancer Stelm Cell Products", Acta Haematol, vol. 101, pp. 97-105, 1999.

Marini, et al. "Purging of Contaminating Breast Cancer Cells from Hematopoietic Stem Cell Grafts by Adenoviral GAL-TEK Gene Therapy and Magnetic Antibody Cell Separation", Clinical Cancer Research, vol. 5, pp. 1557-1568, Jun. 1999.

Damon, et al., "Delayed engraftment of 4-hydroperoxycyclo-phosphamide-purged autologous bone marrow after induction treatment of containg mitoxantrone for acute myelogenous leukemia", Bone Marrow Transplantation, vol. 17, pp. 93-99, 1996.

Wu, et al., "Biological Purging of Breast Cancer Cells Using an Attenuated Replication-competent Herpes Simplex Virus in Human Hematopoietic Stem Cell Transplantation", Cancer Research, vol. 61, No. 7, pp. 3009-3015, Apr. 1, 2001.

Coffey, et al., "Reovirus Therapy of Tumors with Activated Ras Pathway", Science, vol. 282, No. 5392, pp. 1332-1334, Nov. 13, 1998.

Stojdl, et al., "VSV Strains with Defect in their Ability to Shutdown Innate Immunity are Potent Systemic Anti-Cancer Agents", Cancer Cell, (2003) Vol. 4, pp. 263-275.

Fernandez, et al., "Genetically Engineered Vesicular Stomatitis Virus In Gene Therapy: Application for Treatment of Malignant Disease", Journal of Virology, (2002), vol. 76, No. 2, pp. 295-904.

Ebert, et al., "Oncolytic Vesicular Stomatitis Virus for Treatment of Orthotopic Hepatocellular Carcinoma in Immune-Competent Rats", Cancer Research, (2003), vol. 63, pp. 3605-3611.

Ebert, et al., "Systemic Therapy of Experimental Breast Cancer Metastases by Mutant Vesicular Stomatitis Virus in Immune-Competent Mice, Cancer Gene Therapy", (2005), vol. 12, pp. 350-358.

Porosnicu, et al., "The Oncolytic Effect of Recombinant Vesicular Stomatitis Virus is Enhanced by Expression of the Fusion Cytosine Deaminase/Uracil Phosphoribosyltransferase Suicide Gene", Cancer Research, (2003), vol. 63, pp. 8366-8376.

Ahmed, et al., "Sensitivity of Prostate Tumors to Wild Type and M Protein Mutant Vesicular Stomatitis Viruses", Virology, (2004), vol. 330, pp. 34-49.

Balachandran, et al., "Oncolytic Activity of Vesicular Stomatitis Virus is Effective Against Tumors Exhibiting Abberant p53, Ras, or Myc Function and Involves the Induction of Apoptosis", Journal of Virology, (2001), vol. 75, No. 7, pp. 3474-3479.

Belch, et al., "Novel therapeutic strategies in multiple myeloma (MM): Use of shiga-like toxin (SLT) or reovirus to purge myeloma cells", Blood, vol. 92, No. 10 suppl. 1 Part 1-2, pp. 104A-105A, Nov. 1998.

Seth, et al., "Adenovirus-mediated Gene Transfer to Human Breast Tumor Cells: An Approach for Cancer Gene Therapy and Bone Marrow Purging", Cancer Research, vol. 56, No. 6, pp. 1346-1351, Mar. 15, 1996.

Wu, et al., "Bone Marrow Purging of Neuroblastoma by Attenuated Multimutated Herpes Simplex Virus", Proceedings of the American Association for Cancer Research Annual, vol. 39, p. 605, Mar. 1998. (Abstract #4113).

Lichty, et al., "Identification of vesicular stomatitis virus as a leukemolytic agent", Blood, vol. 96, No. 11 Part 2, p. 213b, Nov. 2000.

Stojdl, et al., "Exploiting tumor-specific defects in the interferon pathway with a previously unknown oncolytic virus", Nature Medicine, vol. 6, No. 7, pp. 821-825, Jul. 2000.

Bell, et al., U.S. Appl. No. 09/664,444, "Oncolytic Virus" (filed Sep. 18, 2001).

Sinkovics, et al., J. Clin. Virol. vol. 16, pp. 1-15, 2000.

Baton, et al., Proc. Soc. Exp. iol. Med. vol. 132, pp. 20-26, 1969.

\* cited by examiner

PURGING OF CELLS USING VIRUSES

CROSS-REFERENCE TO PRIOR APPLICATIONS

This is a continuation of U.S. patent application Ser. No. 09/888,626, filed Jun. 26, 2001 now abandoned, the content of which is incorporated herein by reference. This application claims the benefit of U.S. Provisional Patent Application No. 60/214,014, filed Jun. 26, 2000, the content of which is incorporated herein by reference.

FIELD OF THE INVENTION

The subject invention relates to viruses that are able to puree (reduce or eliminate) undesirable cells in a mixture of cells. Undesirable cells can include neoplastic cells. cells mediating graft-versus host diseases, and autoimmune cells. The subject invention also relates to the purging of undesirable cells from bone marrow or peripheral blood cell harvests in the treatment of mammals including cancer patients, transplant recipients, and patients with autoimmune disease.

BACKGROUND OF THE INVENTION

Ex vivo purging techniques have shown limited success for autologous bone marrow or stem cell transplantation in patients with leukemia or other malignancies. One goal of purging bone marrow or peripheral blood progenitor cells (PBPC) is to remove neoplastic cells while having little effect on normal stem cells and hematopoeitic progenitor cells. Transplantation of the purged marrow occurs after myeloablative therapy such as high dose chemotherapy or radiation [see for example, Stuart R. K., 1993, Semin. Oncol. 20(5 Suppl 6):40–54); Hammert L. C. and Ball, E. D., 1997, Curr Opin Hematol 4:423–428; Schneidkraut M. J., et al., 1996, J Hernatother 5:631–646]. Transplantation of any neoplastic cells with the marrow places the patient at risk for relapse of the malignancy (see for example, Rummel SA and Van Zant G, 1994, *J. Hernatother.* 3:213–218; Kvalheim G. et al, 1996, *J Hernatother.* 5:427–436). Methods undergoing current study to selectively kill neoplastic cells include the use of chemotherapeutic agents (such as 4-hydroperoxycyclophosphamide; see for example, Bird J. M., 1996, *Bone Marrow Transplant,* 18:309–313), monoclonal antobodies (see for example, Hammert, L. C. and Ball E. D., 1997, *Blood Rev.,* 11:80–90), photodynamic therapy (see for example, Villeneuve L., 1999, *Biotechnol Appl. Biochem.*30:1–17), and viral vectors such as adenovirus (see for example, Hirai M, et al., 1999, *Acta Haematol.,* 101: 97–105; Marini F. C., et al., 1999, *Clin. Cancer Res.,* 5: 1557–1568). However, recent experiments demonstrated that viable cancer cells remained in the bone marrow or PBPC after therapeutic purging leading to relapse of the malignancy. Another major limitation of current methods of ex vivo purging is the delayed engraftment due to damage to normal stem cells and/or early hematopoietic progenitor cells (Rummel SA and Van Zant G. 1994, *J. Hernatother.* 3:213–218, Damon et al., 1996, *Bone Marrow Transplant,* 17:93–99). Progenitor cells that are actively proliferating are consequently very sensitive to killing by most chemotherapeutic agents including 4-hydroperoxycyclophosphamide. The resultant loss of early progenitor cells causes a prolonged neutropenia and/or thrombocytopenia which places the patient at increased risk for life-threatening infection and/or bleeding. A tumor cytotoxic or cytolytic agent that spares normal hematopoietic cells is an important advance in cancer therapy.

In addition to neoplastic cells, bone marrow or peripheral blood progenitor cell harvests can include other undesirable cells such as autoimmune cells in people with arthritis or multiple sclerosis, for example. Other undesirable cells include those that mediate graft-versus-host disease (e.g., certain T-lymphocytes) in allogeneic transplants. Reduction or elimination of such undesirable cells would be an important in the treatment of cancer and autoimmune diseases.

PCT applications by Roberts et al. (WO/9918799 and PCT US98/21230) relates to the treatment of neoplasms with viruses.

OBJECTS OF THE INVENTION

It is an object of the invention to provide viruses for the reduction or elimination of undesirable cells in mixtures of desirable and undesirable cells.

It is a further object of the invention to provide viruses for the reduction or elimination of neoplastic cells in mixtures of normal and neoplastic cells.

It is a further object to provide viruses for the ex vivo purging of neoplastic cells from normal hematopoetic cells such as bone marrow or peripheral blood progenitor cells.

It is a further object to provide viruses for the ex vivo purging of autoimmune cells from normal cells such as bone marrow or peripheral blood progenitor cells.

It is a further object to provide viruses for the ex vivo purging of cells that mediate graft-versus-host disease from normal hematopoetic cells such as bone marrow or peripheral blood progenitor cells.

It is a further object of the invention to provide a method of treating disease in a mammal by contacting mixtures of desirable hematopoietic cells and undesirable cells with a virus and transplanting such cells into the mammal.

It is a further object of the invention to provide a method of treating cancer in a mammal by contacting harvested cells with a virus and transplanting such purged hematopoietic cells into the mammal after myeloablative treatment.

It is a further object of the invention to provide a method of preventing graft-versus-host diseases by in a mammal by contacting harvested cells with a virus and transplanting such purged hematopoietic cells into the mammal after myeloablative treatment.

It is a further object of the invention to provide a method of treating autoimmune disease in a mammal by contacting harvested cells with a virus and transplanting such purged hematopoietic cells into the mammal after myeloablative treatment It is a further object of the invention to provide a method of treating cancer in a mammal receiving a bone marrow or peripheral blood stem cell transplant comprising the treatment of the transplant with a virus.

SUMMARY OF THE INVENTION

This invention relates to a method of reducing or eliminating undesirable cells in a mixture of desirable cells and undesirable cells by contacting the mixture of cells with a virus.

This invention also relates to a method of reducing or eliminating undesirable cells in a mixture of desirable cells and undesirable cells by contacting the mixture of cells with an RNA virus.

This invention also relates to a method of reducing or eliminating neoplastic cells in an ex vivo mixture of normal hematopoietic cells and neoplastic cells by contacting the mixture with a virus, such as an RNA virus.

This invention also relates to a method for ex vivo purging of neoplastic cells from a bone marrow or peripheral blood stem cell harvest by contacting the harvested cells with a virus, such as an RNA virus.

This invention also relates to a method for ex vivo purging of autoimmune cells from a bone marrow or peripheral blood stem cell harvest by contacting the harvested cells with a virus, such as an RNA virus.

This invention also relates to a method for ex vivo purging of cells that mediate graft-versus-host disease from a population of bone marrow or peripheral blood stem cells by contacting the cell population with a virus, such as an RNA virus.

This invention also relates to a method of treating or preventing disease such as cancer in a mammal comprising: a) removing bone marrow or peripheral blood cells from said mammal, b) contacting said bone marrow or peripheral blood cells ex vivo with a virus, such as an RNA virus, c) performing myeloablative treatment on said mammal, and d) transplanting into said mammal the purged hematopoietic cells of step b.

This invention also relates to a method of treating cancer in a mammal receiving a bone marrow or peripheral blood progenitor cell transplant comprising contacting the harvested cells of the transplant with a virus, such as an RNA virus, and administering the purged cells to said mammal.

This invention also relates to a method of treating autoimmune disease in a mammal receiving a bone marrow or peripheral blood progenitor cell transplant comprising contacting the harvested cells of the transplant with a virus, such as an RNA virus, and administering the purged cells to said mammal.

This invention also relates to a method of preventing graft-versus-host disease in a mammal receiving a bone marrow or peripheral blood progenitor cell transplant comprising contacting the harvested cells of the transplant with a virus, such as an RNA virus, and administering the purged cells to said mammal.

DETAILED DESCRIPTION OF THE INVENTION

The present invention relates to the discovery of viruses and the use of viruses for the reduction or elimination of undesirable cells such as neoplastic cells from a mixture of desirable cells and undesirable cells. This invention provides viruses and methods for the purging (reducing or eliminating) of undesirable cells from normal cells using viruses. Undesirable cells in hematopoeitic cell transplants that are removed by viruses in the present invention include neoplastic cells, autoimmune cells (such as in the case of rheumatoid arthritis or multiple sclerosis), and cells which mediate graft-versus-host disease. Treatment of the mammal consists of a) removing bone marrow or peripheral blood cells from said mammal, b) contacting said bone marrow or peripheral blood cells ex vivo with a virus, c) performing myeloablative treatment on said mammal, and d) transplanting into said mammal the purged hematopoeitic cells of step b).

Methods of the Invention

Purging of Neoplastic Cells

Incubation of mixtures of normal cells and neoplastic cells with viruses result in the selective killing of the neoplastic cells and not the normal cells. Effective means of purging neoplastic cells from hematopoietic cells can be used in the treatment of cancer in mammals with autologous bone marrow or peripheral blood stem cell transplantation. For example, bone marrow or peripheral blood stem cells from a mammal with a neoplasm is contacted with a virus prior to transplant to prevent relapse from the neoplasm. Neoplastic cells that can be purged by the methods of the invention include, but are not limited to, (1) leukemia, (2) lymphoma, (3) carcinomas such as breast cancer, lung cancer, colon cancer, prostate cancer, and pancreatic cancer, (4) sarcomas, and (5) cancers of neuroepithelial origin such as melanoma and neuoblastoma.

Diverse viruses such as RNA viruses [such as, but not limited to vesicular stomatitis virus (VSV), Newcastle disease virus (NDV), and reovirus] can be used to purge neoplastic cells from normal hematopoietic cells. Normal hematopoeitc cells are resistant to infection by many viruses including RNA viruses. As an example, normal human marrow cells are resistant to infection by VSV, a rhabdovirus, as determined by both infectious virus production and by viability. Normal marrow cells from two donors produced no infectious virus even when infected at a high multiplicity of infection (e.g., 10 plaque forming units (pfu)/cell; see Example 1). Infected bone marrow cultures were indistinguishable from mock-infected cultures in their ability to form the normal spectrum of hematopoietic cell types following in vitro culture in methylcellulose. As another example, CD34+ enriched normal human marrow were resistant to infection by NDV, a virus from another family (paramyxovirus); see Roberts et al., WO/9918799.

Many types of neoplastic cells are highly sensitive to cell killing by many viruses including RNA viruses. As an example using VSV, acute myelogenous leukemia cell lines OCI/AML3, OCI/AML4 and OCI/AML5 were highly susceptible to VSV infection with 0.05 pfu/cell killing 50% of the cells at 24 hours and as little as 0.0003 pfu/cell killing 50% at 48 hours (Example 1). The VSV Indiana serotype used in this experiment was propagated and harvested from murine L929 cells. As another example, diverse tumor cell types were shown to be sensitive to VSV including ovarian carcinoma, fibrosarcoma, lung carcinoma, melanoma, prostate carcinoma, and leukemia cells (see Example 3). NDV also kills most human neoplastic cells (see Roberts et al., WO/9918799). Reovirus type 3 killed human neoplastic fibrosarcoma cells but not normal fibroblasts (Example 4).

The selective elimination of neoplastic cells from a co-culture with normal hematopoietic cells can be achieved with a variety of viruses. For example, in co-cultures of leukemic OCI/AML3 cells with normal bone marrow cells (at a 1:9 ratio and at a 1:3 ratio) VSV killed all of the leukemia cells while having little if any effect on the normal hematopoeitic cells (Example 2). The VSV Indiana serotype used in this experiment was propagated and harvested from murine L929 cells. These data show the selective destruction of leukemic cells in a mixed population of normal marrow and the utility of viruses such as VSV in bone marrow purging. As another example in selective elimination of neoplastic cells in a mixed culture of normal cells was shown with NDV. NDV strain PPMK107, a triple plaqued purified isolate of the meosogenic NDV strain MK107, selectively killed human oral carcinoma cells in a mixed culture with normal fibroblasts (see Roberts et al., WO/9918799).

Purging of Cells Mediating Graft-versus-host Disease.

Incubation of mixtures of undesirable cells such as T lymphocytes causing graft-versus-host disease and desirable cells with viruses result in the selective killing of the undesirable cells. Effective means of purging such marrow or peripheral blood cells can be used in the prevention of graft-versus-host disease in mammals.

Purging of Cells Mediating Autoimmune Disease.

Incubation of mixtures of autoimmune cells causing autoimmune disease and desirable cells with viruses result in the selective killing of the autoimmune cells. Effective means of purging of such undesirable cells can be used in the treatment of autoimmune disease such as rheumatoid arthritis and multiple sclerosis.

Screening of Undesirable Cells.

Undesirable cells of the present invention can include neoplastic cells with chromosomal deletions or rearragements of a gene, or genes, encoding proteins or modulators of the cellular interferon response or harbor an otherwise defective interferon response (Colamonici OR, et al, 1992, *Blood*, 80:744–749; Heyman M, et al, 1994, *Leukemia*, 8:425–434; Billard C, et al, 1986, *Blood*, 67:821–826). The suspended nature of bone marrow or PBPC populations allows for the facile use of fluorescence activated cell sorting (FACS) analysis in the determination of the interferon responsive state of the cell. Probes for interferon responsiveness include chromosomal hybridization probes for gene deletions or rearragements, and probes, such as antibodies, for the analysis of cellular receptors and components of signal transduction pathways involved in the cellular response to interferon.

Compounds of the Invention

The viruses of the present invention are capable of distinguishing undesirable cells such as neoplastic cells from desirable cells such as normal hematopoeitic cells. RNA viruses of this present invention include, but are not limited to (1) single-stranded viruses including those of negative-sense RNA viruses and positive-sense RNA viruses, and (2) double-strand RNA viruses. Single strand, negative-sense RNA viruses of the invention include, but are not limited to, those non-segmented virus families such as rhabdoviruses [(for example, vesicular stomatitis virus (VSV)] and paramyxoviruses [for example, Newcastle disease virus (NDV) and human parainfluenza virus type 3]. Single strand, positive-sense RNA viruses of the present invention include, but are not limited to picornaviruses [for example, rhinovirus], and togaviruses [for example, Sindbis virus]. Double-strand RNA virus families of the invention include reoviruses. Replication-competent and replication-incompetent RNA viruses are included in the invention.

Included in the present invention are the "interferon-sensitive viruses" described in Roberts et al., WO/9918799, which is herein incorporated by reference in its entirety. These viruses selectively replicate and kill neoplastic cells based on the selective deficiency in these cells of an IFN-mediated antiviral response. In addition to RNA viruses, included among the "interferon-sensitive viruses" are VA1-mutants of adenovirus, a DNA virus.

The rhabdovirus family consist of closely related enveloped, non-segmented negative-sense, RNA viruses and include the following genera that infect animals: (1) Vesiculovirus genus (e.g, vesicular stomatitis virus, VSV); (2) the Lyssavirus genus (e.g, rabies virus); and (3) the Ephemerovirus genus [Dietzschold B et al.,1996. Rhabdoviruses. In: *Fields Virology*, $3^{rd}$ Edition, (eds. Fields B. N., et al.), pp1 137–1159].

In an especially advantageous embodiment according to the present invention, the rhabdovirus is vesicular stomatitis virus (VSV). Several serologically distinct VSV strains have been identified along with a multitude of characterized mutants. The natural hosts of VSV include insects, rodents and domestic farm animals. In general, very few North American people have come in contact with the virus with most human infections occurring in laboratory personnel and farmers. In humans, infections are either asymptomatic or manifested as flu-like symptoms. VSV strains include, but are not limited to, Indiana, New Jersey, Priv. Coccal and Chandipura. While the examples disclosed herein relates to VSV Indiana, it is to be understood that one of skill in the art, by following the methods outlined in this document, will be readily be able to screen other VSV strains and derivatives of VSV including mutants of VSV that selectively kill neoplastic cells.

The paramyxovirus family of non-segmented negative-sense RNA viruses comprises three genera: (1) paramyxoviruses inluding Newcastle disease virus (NDV); (2) measles-like viruses (morbilli viruses); and (3) respiratory syncytial viruses (pneuviruses). NDV is an advantageous virus according to the present invention. NDV is catagorized into three distinct classes according to the effects on chickens and chicken embros. "Low virulence" strains are referred to as lentogenic and take 90 to 150 hours to kill chicken embryos at the minimum lethal dose (MLD); "moderate virulence" strains are referred to as mesogenic and take 60 to 90 hours to kill chicken embryos at the MLD; "high virulence" strains are referred to as velogenic and take 40 to 60 hours to kill chicken embryos at the MLD. See, e.g., Hanson and Bradley, 1955 (Science, 122:156–157), and Diardiri et al., 1961 (Am J Vet Res 9:918–920). All three classes are useful, including, advantageously, mesogenic strains of NDV such as MK107.

In an especially advantageous embodiment according to the present invention, the double-strand RNA virus is reovirus. In a further advantageous embodiment according to the present invention, the reovirus is reovirus type 3.

In another advantageous embodiment of the invention, RNA viruses capable of replicating in neoplasms deficient in the expression of subtilism-related proteases are used. Human parainfluenze virus type 3 is a virus of this type.

For certain purposes, it is desirable to obtain a clonal virus to ensure or increase genetic homogeneity of particular virus strain and to remove defective interfering particles. Removal of defective interfering particles allows for increased purity in the final product as assessed by the number of total virus particles per infectious particle. Clonal virus can be generated by plaque purification or by other means as described in Roberts et al., WO/9918799.

In another embodiment of the invention, the virus is genetically modified, as for example, to increase its selectivity for neoplastic cells. Methods of genetic manipulation of rhabdoviruses such as VSV are well established (Roberts A., and J. K. Rose, Virology, 1998, 247:1–6) making it possible to alter the genetic properties of the virus.

Furthermore, standard techniques well known to one of skill in the art can be used to genetically modify VSV and introduce desired genes within the VSV genome to produce recombinant VSVs (e.g., Sambrook et al., 1989, A Laboratory Manual, New York, Cold Spring Harbor Press). In one embodiment of the invention, the G protein of VSV can be modified to produce fusions that target specific sites on rumor cells. In another embodiment of the invention, the VSV is genetically altered to express one or more suicide genes capable of metabolizing a prodrug into a toxic metabolite thereby permitting VSV infected tumor cells to be killed by administration of a prodrug. VSV engineered to express the herpes virus thymidine kinase or the cytosine deaminase gene can be used to convert ganciclovir or 5-FC, respectively, into a toxic compound. However, it is understood that other suicide genes can also be employed.

Formulation and Administration

An advantageous embodiment of the invention relates a kit for use in the ex vivo purging of undesirable cells from a mixture of desirable and undesirable cells. The kit includes premeasured amounts of formulated virus, or viruses, appropriate to treat a mixture containing a certain number of desirable and undesirable cells. Advantageous formulations include excipients that stabilize the virus against loss of infectivity, or boost the viability or survival of the desirable cells. A more advantageous kit allows for the contacting of the virus formulation with the target mixture of cells to occur in an aseptic step without the need for biocontainment equipment. An example of such a device is a compartmentalized collection container for the target mixture of cells that contains the pre-measured virus in a separate compartment. Creation of a patent pathway between the compartments allows contact between the virus, the target cell population, and one or more excipients. Contact with the virus and excipients, if separate, can occur simultaneously, or sequentially. A further advantageous embodiment of the invention is a type of compartmentalized container that maintains the optimum temperature for virus cell interaction during the time of contact between the virus, or viruses, and the target mixture of desirable and undesirable cells. Another advantageous embodiment of the invention relates to a kit that allows for the separation of the contacted mixture of cells from the virus, excipients, or both after an appropriate amount of time. The appropriate amount of contact time would be known or determined by someone skilled in the art.

Suitable formulations for viruses of the present invention include those listed for viruses used in the treatment of neoplasms (Roberts, et al, 1999, PCT WO9918799). In addition, advantageous formulations include compounds or biologicals that have one or more of the following activities on the desirable cells in the mixture of desirable and undesirable cells: differentiating, proliferating, sparing, stimulating, protecting, and inducing quiescence. For example, compounds and biologicals of these types include, cytokines, peptide regulators of cell cycling, interleukins, growth factors, energy sources, vitamins and electrolytes. Additional desirable excipients include cryoprotective compounds.

An effective amount of virus in the invention is to be used for the reduction or elimination of the undesirable cells with the maintenance of the desirable cells. It is understood by those skilled in the art that the amount of virus to be used for the reduction or elimination of the undesirable cells will vary depending upon the virus selected, the type and amount of undesirable cells, and the type and amount of desirable cells to be maintained. For example, VSV is used at 0.00001 to 10 plaque forming units (pfu) per cell, and more advantageously at 0.0003 to 10 pfu per cell.

In another advantageous embodiment of the invention, the virus is used to contact the mixture of neoplastic cells and normal cells which are treated before, during or after contact with interferon. Interferon allows for enhanced protection of normal cells (see Example 3 and see Roberts et al., WO/9918799). The interferon (IFN) is selected from the group-class I (alpha, beta and omega) and class II (gamma), and recombinant versions and analogs thereof as discussed in, for example, Sreevalsoun, T., 1995 (In: Biologic Therapy of Cancer, second edition, edited by V. T. DeVita, Jr., et al., J. B. Lippincott Company, Philadelphia, pp347–364).

In another advantageous embodiment of the invention, the virus is used to contact the mixture of neoplastic cells and normal cells which are treated with a chemotherapeutic agent before during or after contact with said virus. The chemotherapeutic agent is used to further reduce the viability of the neoplastic cells.

The following examples are illustrative, but not limiting of the methods and compositions of the present invention. Other suitable modifications and adaptations of a variety of conditions and parameters normally encountered in clinical therapy which are obvious to those skilled in the art are within the spirit and scope of this invention.

EXAMPLE 1

Selective Killing of Leukemia Cells and Not Normal Marrow Cells by Vesicular Stomatitis Virus as Determined in Separate Cell Cultures The VSV Indiana serotype was plaque purified on mouse L929 cells. An individual plaque was used to infect a monolayer of L929 cells and 18 hours later the supernatant havested and subjected to centrifugation at 6,000×g for ten minutes. The clarified supernatant was then filtered through a 0.2 micron filter (Millipore) and then titered on L cells and stored at −80° C. in aliquots. Individual aliquots of virus was used only once. Normal bone marrow cultures from two separate healthy donors were resistant to infection by this Indiana serotype of vesicular stomatitis virus (VSV). Normal bone marrow cells produced no infectious VSV particles, even when infected at a multiplicity of infection of 10 pfu/cell. Moreover, the infected bone marrow cultures were indistinguishable from mock-infected cultures in their ability to form the normal spectrum of hematopoietic cell types following in vitro culture in methylcellulose. In contrast, AML cell lines OCI/AML3, OCI/AML4 and OCI/AML5 were highly susceptible to VSV infection with 0.05 pfu/cell killing 50% of the cells at 24 hours and as little as 0.0003 pfu/cell killing 50% at 48 hours.

EXAMPLE 2

Selective Killing of Leukemia Cells by Vesicular Stomatitis Virus in Mixed Cultures Containing Normal Marrow Cells The VSV Indiana serotype used in this example was prepared as indicated in Example 1 In co-cultures of leukemic OCI/AML3 cells mixed with normal bone marrow cells (1:9 ratio) VSV had selective oncolytic properties. In this experiment (Table 1), co-cultures were infected with VSV at a multiplicity of infection of 1 plaque forming unit (pfu)/cell or 5 pfu/cell for 24 hours and then plated in methylcellulose with or without growth factors. In the presence of growth factors, both normal marrow and tumor cells grew while only OCI/AML3 cells formed colonies in the absence of growth factors. Colony counts were performed after 14 days (Table 1) and demonstrated a complete ablation of growth factor-independent leukemic cells and sparing of normal bone marrow progenitors. Identical results were observed when a 1:3 mixture of OCI/AML3 cells and normal marrow were used. This data shows the selective destruction of leukemic cells in a mixed population of normal marrow and the utility of VSV in ex vivo bone marrow purging.

TABLE 1

Selective killing of acute myelogenous leukemia (AML) cells co-cultured with normal bone marrow. Colonies per dish (receiving $10^4$ cells) observed two weeks after VSV infection are tubulated below for neoplastic cells (leukemia) and normal hematopoeitic cells (neutrophil, mixed, and monocyte).

| Colony Type | Multiplicity of Infection | | |
|---|---|---|---|
| | 0.0 | 1.0 | 5.0 |
| Leukemic | 172 | 0 | 0* |
| Neutrophil | 12 | 7 | 5 |
| Mixed | 6 | 3 | 4 |
| Monocyte | 10 | 7 | 5 |

*No leukemic colonies were detected on the growth factor minus dishes even when $10^5$ cells were plated per dish.

EXAMPLE 3

VSV Selectively Grows in and Kills Neoplastic Cells Compared to Normal Cells as Determined in Separate Cell Cultures.

A variety of normal and transformed cell lines were either untreated or pre-treated with 100 units of IFN-alpha infected with VSV Indiana at an MOI of 0.1 pfu/ml and incubated for 18 hours at 37° C. (Table 2). Culture media from each sample was titred for VSV production. Pre-treatment of the normal cell cultures with interferon reduced viral production to <1000 infectious viral particles per ml., while tumor cell lines continued to produce copious amounts of virus particles ($10^{5-10^8}$ plaque forming units per ml.). In tumor cells, a more rapid and fulminant growth of VSV was observed than in primary normal cell cultures of fibroblastic or epithelial origin. The differences between the various cell types was reflected not only in production of virus particles, but also in the cytopathic effect (cpe) observed at the microscopic level.

TABLE 2

Virus yield of VSV after overnight infection of various cell lines either untreated or treated with IFN

| | Viral Titre (pfu/ml) | |
|---|---|---|
| Cell Line | Untreated | IFN-α |
| OSF7 (primary normal human fibroblast) | $1 \times 10^6$ | <10 |
| OSF12 (primary normal human fibroblast) | $2 \times 10^5$ | <10 |
| OSF16 (primary normal human fibroblast) | $1 \times 10^5$ | <10 |
| PrEC (primary normal human prostate epithelium) | $8 \times 10^6$ | <10 |
| HOSE (primary normal human ovarian surface epithelium) | $1 \times 10^7$ | <1000 |
| A2780 (human ovarian carcinoma) | $2 \times 10^8$ | $1 \times 10^7$ |
| OVCA 420 (human ovarian carcinoma) | $1 \times 10^8$ | $3 \times 10^6$ |
| C13 (human ovarian carcinoma) | $1 \times 10^8$ | $1 \times 10^5$ |
| LC80 (human lung carcinoma) | $2 \times 10^9$ | $6 \times 10^7$ |
| SK-MEL3 (human melanoma) | $1 \times 10^9$ | $1 \times 10^9$ |
| LNCAP (human prostate carcinoma) | $4 \times 10^9$ | $5 \times 10^9$ |
| HCT116 (human colon carcinoma) | $1 \times 10^9$ | $2 \times 10^9$ |
| 293T (HEK cells transformed with T antigen and Ad virus E1A) | $1 \times 10^8$ | $8 \times 10^7$ |

EXAMPLE 4

Selective Killing of Neoplastic Cells and Not Normal Fibroblast Cells by Reovirus Type 3 in Separate Cell Cultures Human tumor cells (HT1080 fibrosarcoma) and normal cells (CCD922sk, normal human skin fibroblasts) were grown to approximately 80% confluence in 24 well tissue culture dishes. Growth medium was removed and PPVR-824, a plaque purified clone of human reovirus type III, Dearing strain, was added at 1E+6 plaque forming units (PFU)/well, to 10 PFU/well in 10 fold dilutions (Exp 1) or at 7.2E+7 PFU/well, and 10-fold dilutions ranging from $10^7$ 1 to 100 PFU/well (Exp II). Controls wells with no virus added were included on each plate. Virus was adsorbed for 90 minutes on a rocking platform at 37° C. At the end of the incubation period, the viral dilutions were removed and replaced by 1 ml of growth medium. Plates were then incubated for 5 days at 37° C. in 5% CO2. Cytotoxicity was quantified by using a calorimetric MTT (2-[4,5-dimethylthiazol-2-Yl]-2,5-diphenyl tetrazolium bromide) assay (Cell Titer 96, catalog #G4000, Promega Corporation, Madison Wis. 53711) monitored at 570 nm, that detects mitochondrial enzyme activity (Mosman, T., 1983, J. Immunol. Methods 65:55). The viability in the virus treated wells was expressed as a percent of the activity in untreated control wells. The data was plotted graphically as PFU/well vs. viability as a percent of control. The IC50 was calculated as the amount of virus in PFU/well causing a 50% reduction in the amount of viable. The neoplastic cells were orders of magnitude more sensitive to killing by PPVR-824 (Table 3).

TABLE 3

Selective Killing of Neoplastic Cells and Not Normal Fibroblast Cells by Reovirus Type 3 in Separate Cell Cultures

| | Normal Fibroblast (CCD922sk), IC50 | Neoplastic Cell (HT1080), IC50 |
|---|---|---|
| Expt I | >1.0E+06 | 125 |
| Expt II | >7.2E+07 | 417 |

The foregoing examples are intended as illustrative of the present invention but not limiting. Numerous variations and modifications can be effected without departing from the true scope of the invention.

What is claimed is:

1. A method of reducing or eliminating neoplastic cells in an ex vivo mixture of normal, hematopoeitic cells and neoplastic cells comprising contacting said mixture with a vesicular stomatitis virus, wherein the mixture is a suspension.

2. A method as in claim 1 wherein said neoplastic cells are leukemia cells.

3. A method as in claim 1 wherein said hematopoeitic cells are marrow cells.

4. A method as in claim 1 wherein said hematopoeitic cells are peripheral blood cells.

5. A method as in claim 1 wherein said virus is replication-competent.

6. A method as in claim 1 wherein said neoplastic cells are lymphoma cells.

7. A method as in claim 1 further comprising administering a chemotherapeutic agent to the mixture before, during or after contacting with said virus.

8. A method of treating cancer in a mammal comprising:
   a) removing bone marrow or peripheral blood cells from said mammal as a suspension,
   b) incubating said suspension of bone marrow or peripheral blood cells ex vivo with an effective amount of a vesicular stomatitis virus to yield purged bone marrow or peripheral blood cells,
   c) performing myeloablative treatment on said mammal, and
   d) transplanting into said mammal the purged bone marrow or peripheral blood cells of step b.

9. A method as in claim 7 wherein said myeloablative treatment is high dose chemotherapy.

10. A method of treating cancer in a mammal receiving a transplant of bone marrow or peripheral blood stem cells comprising purging said bone marrow or peripheral blood stem cells by incubating a suspension of said bone marrow or peripheral blood stem cells ex vivo with an effective amount of a vesicular stomatitis virus, and administering the resulting purged cells to said mammal.

* * * * *